(12) United States Patent
Hoernig et al.

(10) Patent No.: US 12,220,267 B2
(45) Date of Patent: Feb. 11, 2025

(54) COMPUTER-IMPLEMENTED METHOD FOR DETERMINING AN ABNORMAL STRUCTURE

(71) Applicant: Siemens Healthineers AG, Forchheim (DE)

(72) Inventors: Mathias Hoernig, Moehrendorf (DE); Christian Huemmer, Lichtenfels (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 177 days.

(21) Appl. No.: 17/953,764

(22) Filed: Sep. 27, 2022

(65) Prior Publication Data

US 2023/0111463 A1 Apr. 13, 2023

(30) Foreign Application Priority Data

Sep. 29, 2021 (EP) ..................................... 21199847

(51) Int. Cl.
  *A61B 6/03* (2006.01)
  *G06T 7/00* (2017.01)
(52) U.S. Cl.
  CPC ............ *A61B 6/032* (2013.01); *G06T 7/0012* (2013.01); *G06T 2207/10116* (2013.01); *G06T 2207/20081* (2013.01)
(58) Field of Classification Search
  CPC .................. A61B 6/032; G06T 7/0012; G06T 2207/10116; G06T 2207/20081; G06T 2207/20084; G06T 2207/30068; G06T 2207/30096
  See application file for complete search history.

(56) References Cited

U.S. PATENT DOCUMENTS

| 7,671,342 | B2 | 3/2010 | Bani-Hashemi et al. |
| 10,957,079 | B2 | 3/2021 | Teare |
| 10,977,790 | B2 * | 4/2021 | Fieselmann .......... A61B 5/7264 |
| 11,289,320 | B2 * | 3/2022 | Pringle ............... H01J 49/0004 |
| 11,694,319 | B2 * | 7/2023 | Kang ..................... G06V 10/82 382/100 |
| 11,841,923 | B2 * | 12/2023 | Jiang .................... G06V 10/454 |

(Continued)

FOREIGN PATENT DOCUMENTS

DE 102020212105 A1 3/2022

OTHER PUBLICATIONS

Yang He et al.: "Deep learning for dual-energy X-ray computed tomography", Augusta University; 2017.

(Continued)

*Primary Examiner* — Vijay Shankar
(74) *Attorney, Agent, or Firm* — Harness, Dickey & Pierce, P.L.C.

(57) ABSTRACT

A compute-implemented method for determining an abnormal structure in an examination region in conjunction with an X-ray recording of an X-ray system, comprising receiving input data, the input data relating to an X-ray recording data set of the X-ray recording having multiple data channels; applying a trained function to the input data, the trained function being based on a machine learning method and applied to at least two data channels to determine the abnormal structure and generate output data; and providing the output data, the output data including an abnormal structure of the examination region.

15 Claims, 3 Drawing Sheets

(56) References Cited

U.S. PATENT DOCUMENTS

2019/0021677 A1    1/2019    Grbic et al.
2021/0287799 A1    9/2021    Guendel et al.
2021/0304361 A1    9/2021    Huemmer et al.

OTHER PUBLICATIONS

Lee, Hyunkwang et al. "Fully Automated Deep Learning System for Bone Age Assessment", J Digit Imaging, 2017, DOI: 10.1007/s10278-017-9955-8.

Guendel, S. et al., Learning to recognize abnormalities in chest X-rays with location-aware dense networks, arXiv 1803.04565; Mar. 12, 2018; 9 pp; 2018.

Lyu Tianling et al.: "Estimating dual-energy CT imaging from single-energy CT data with material decomposition convolutional neural network", Medical Image Analysis vol. 70, May 2021, 102001.

Bruns St. et al.: „Deep Learning from Dual-Energy Information for Whole-Heart Segmentation in Dual-Energy and Single-Energy Non-Contrast-Enhanced Cardiac CT, , https://arxiv.org/abs/2008.03985; 2008.

KA Imaging: "KA Imaging's X-Ray Detector Allows Any X-Ray System to Be Upgraded to Dual-Energy" Date of screenshot: Oct. 21, 2021.

Li, Zhe et al. "Thoracic Disease Identification and Localization with Limited Supervision" 2018.

Santos M.K. et al.: "Artificial intelligence, machine learning, computer-aided diagnosis, and radiomics: advances in imaging towards to precision medicine", Radiol. Bras., 2019, 52(6), 387-396.

Oakden-Rayner L.: The Rebirth of CAD: How Is Modern AI Different from the CAD We Know?, Radiology artificial intelligence, vol. 1, No. 3, 2019.

Chen, Matthew: "Automated Bone Age Classification with Deep Neural Networks", 2016, http://cs231n.stanford.edu/reports/2016/pdfs/310_Report.pdf.

Lee S. Choi J.H. et al..: "Noise reduction approach in pediatric abdominal CT combining deep learning and dual-energy technique", European Radiology vol. 31, pp. 2218-2226 (2021).

* cited by examiner

COMPUTER-IMPLEMENTED METHOD FOR DETERMINING AN ABNORMAL STRUCTURE

CROSS-REFERENCE TO RELATED APPLICATION(S)

The present application claims priority under 35 U.S.C. § 119 to European Patent Application No. EP 21199847.1, filed Sep. 29, 2021, the entire contents of which are incorporated herein by reference.

FIELD

One or more example embodiments relates to a computer-implemented method for determining an abnormal structure and an X-ray system, a computer program product and a computer readable medium.

BACKGROUND

Computer aided diagnosis (CAD) that uses artificial intelligence (AI) is a known tool in identifying or assessing suspicious regions and/or probabilities of the presence of dedicated discoveries in medical images. Examples are known from Santos, M. K., Ferreira Júnior, J. R., Wada, D. T., Tenório, A., Barbosa, M., & Marques, P. (2019). Artificial intelligence, machine learning, computer-aided diagnosis, and radiomics: advances in imaging towards to precision medicine. Radiologia brasileira, 52(6), 387-396. https://doi.org/10.1590/0100-3984.2019.0049 and L. Oakden-Rayner: "The Rebirth of CAD: How Is Modern AI Different from the CAD We Know?, Radiology: Artificial Intelligence 2019; 1(3):e180089. https://doi.org/10.1148/ryai.2019180089.

The use of AI-based CAD algorithms is hitherto limited to medical images that have been recorded using single layered X-ray (flat panel) detectors, for example via a-SI technology.

The publication U.S. Pat. No. 7,671,342 B2 discloses an X-ray detector comprising multiple layers, for example multiple layers of fluorescent screens and/or detectors or detection layers. Some X-ray beams that penetrate a layer are detected in another layer or are converted into light energy. In this manner for example, a phosphorus screen is located upstream and a further phosphorus screen is located downstream of the detector circuit. The light that is generated in each of the fluorescent screens is detected by the same detector circuit. A further example are multiple layers of fluorescent screens and associated detector circuits. Some X-ray beams that penetrate a layer can be detected in another layer. It is possible to detect both highly energetic X-ray beams, which are connected to megavoltage sources, as well as X-ray beams having lower or higher energy. Moreover, a dual energy X-ray detector is known from the article "KA IMAGING'S X-RAY DETECTOR ALLOWS ANY X-RAY SYSTEM TO BE UPGRADED TO DUAL-ENERGY" (https://www.kaimaging.com/blog/ka-imagings-x-ray-detector-allows-any-x-ray-system-to-be-upgraded-to-dual-energy/).

The X-ray beam or the photons can be converted into electrical pulses in direct converting X-ray detectors by a suitable converter material. It is possible to use for example CdTe, CZT, CdZnTeSe, CdTeSe, CdMnTe, InP, TlBr2, HgI2, GaAs or others as the converter material. The electrical pulses are evaluated by an electronic evaluating system, for example an integrated switching circuit (application specific integrated circuit, ASIC). In numerous X-ray detectors incident X-ray radiation is measured by counting the electrical pulses that are triggered by the absorption of X-ray photons in the converter material. The level of the electrical pulse is in general proportional to the energy of the absorbed X-ray photons. As a consequence, a spectral information can be extracted by the comparison of the level of the electrical pulse with a threshold value.

From a clinical point of view, multi-layered detectors render it possible to create a series of diagnostic images from recorded X-ray information of different energy at identical points in time. The utilization of multiple detector layers renders possible a quantitative analysis of materials via energy-resolved ("spectral") measurements and renders possible a precise detection of potential (findings) discoveries by the provision of diagnostic images for materials having different characteristics in the image (for example differentiation of bones and soft tissue). The image set that is generated (for example two images for a dual energy system) is inspected by clinical experts in order to make a judgement regarding the state of health of the patient and possible treatments.

From an algorithmic point of view, it is possible to use complementary information in input data for AI-based CAD algorithms however hitherto the complementary data is based on one input image without a possibility of taking into account multiple physical detection layers.

AI-based algorithms can be used in order to connect sinograms from dual energy CT to monoenergetic sinograms (cf. Yang, H., Cong, W., & Wang, G. (2017). Deep learning for dual-energy X-ray computed tomography. In Proceedings of The 14th International Meeting on Fully Three-Dimensional Image Reconstruction in Radiology and Nuclear Medicine (pp. 864-869)9 in order to reduce noise (cf. Lee, S., Choi, Y. H., Cho, Y. J. et al. Noise reduction approach in pediatric abdominal CT combining deep learning and dual-energy technique. Eur Radiol 31, 2218-2226 (2021). https://doi.org/10.1007/s00330-020-07349-9), to assess dual energy data from single energy data (cf. Tianling Lyu, Wei Zhao, Yinsu Zhu, Zhan Wu, Yikun Zhang, Yang Chen, Limin Luo, Shuo Li, Lei Xing, Estimating dual-energy CT imaging from single-energy CT data with material decomposition convolutional neural network, Medical Image Analysis, Volume 70, 2021, 102001, ISSN 1361-8415, https://doi.org/10.1016/j.media.2021.102001.) and in order to assess non-contrast enhanced images (cf. Steffen Bruns et al: "Deep Learning from Dual-Energy Information for Whole-Heart Segmentation in Dual-Energy and Single-Energy Non-Contrast-Enhanced Cardiac CT", https://arxiv.org/abs/2008.03985).

SUMMARY

At the basis of one or more example embodiments of the present invention lies the problem of improving the accuracy of an AI-based CAD algorithm based on the recording data in order to render possible an increased reliability in the CAD discoveries.

The object of one or more example embodiments of the present invention is to disclose an apparatus X and a method X that render it possible to improve the accuracy of an AI-based CAD algorithm.

The object is achieved in accordance with one or more example embodiments of the present invention by a computer-implemented method for determining an abnormal structure as claimed, a determining unit as claimed, an X-ray system as claimed, a computer program product as claimed and a computer readable medium as claimed.

Moreover, one or more example embodiments of the present invention relates to a computer readable medium on which program sections, which can be read and executed by a computer unit, are stored in order to perform all the steps of a method in accordance with one or more example embodiments of the present invention if the program sections are executed by the determining unit in accordance with one or more example embodiments of the present invention or the X-ray system in accordance with one or more example embodiments of the present invention.

One or more example embodiments relates to a computer-implemented method for determining an abnormal structure in an examination region in conjunction with an X-ray recording of an X-ray system, comprising receiving input data, the input data relating to an X-ray recording data set of the X-ray recording having multiple data channels; applying a trained function to the input data, the trained function being based on a machine learning method and applied to at least two data channels to determine the abnormal structure and generate output data; and providing the output data, the output data including an abnormal structure of the examination region.

According to one or more example embodiments, the receiving the input data includes providing a recording image data set for each data channel.

According to one or more example embodiments, the data channels relate to data sets that are different from one another from the group of: a soft part data set, a bone data set, a native image data set, a contrast medium data set, an energy region data set or multiple energy region data sets that are different from one another.

According to one or more example embodiments, the X-ray recording data set is recorded using a multi-layered X-ray detector or a photon-counting X-ray detector.

According to one or more example embodiments, the input data comprises at least one of: complementary information in the data channels, spectral or material-resolving information, or information based on a recombination of image data of the data channels.

According to one or more example embodiments, the applying applies the trained function to the at least two data channels simultaneously.

According to one or more example embodiments, the trained function is based on a deep learning method for red-green-blue (RGB) images.

According to one or more example embodiments, three data channels are used.

According to one or more example embodiments, the method further includes applying image processing to the X-ray recording data set prior to applying the trained function.

According to one or more example embodiments, the output data comprises a position of a lesion, a position of a microcalcification, a position of a landmark, a distance or an angle.

According to one or more example embodiments, a determining apparatus configured to determine an abnormal structure in an examination region in conjunction with an X-ray recording of an X-ray system, the determining apparatus comprising a first interface configured to receive input data, the input data relating to an X-ray recording data set of the X-ray recording having multiple data channels; a computer unit configured to apply a trained function to at least two data channels to determine the abnormal structure and generate output data, the trained function being based on a machine learning method; and a second interface configured to provide the output data, the output data including the abnormal structure of the examination region.

According to one or more example embodiments, an X-ray system has the determining apparatus.

According to one or more example embodiments, a non-transitory computer program product has a computer program that, when executed by a control facility of an X-ray system, are configured to cause the X-ray system to perform the method of claim 1.

According to one or more example embodiments, a non-transitory computer readable medium has program sections that, when executed by a computer unit, cause the computer unit to perform the method of claim 1.

BRIEF DESCRIPTION OF THE DRAWINGS

Exemplary embodiments of the present invention are further explained below with reference to drawings. In this case in the drawing.

DETAILED DESCRIPTION

Figure 1:
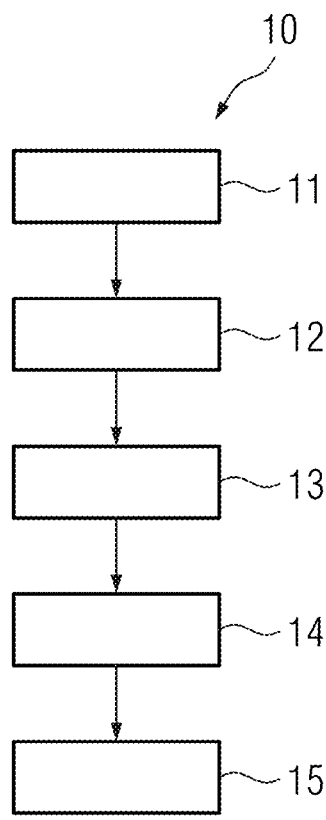
FIG. 1 shows schematically an illustration of a method in accordance with the invention in a first embodiment.

One or more example embodiments of the present invention relates to a computer-implemented method for determining an abnormal structure in an examination region in conjunction with an X-ray recording of an X-ray system having the following steps of receiving, applying and providing. In the receiving step, input data is received, wherein the input data relates to an X-ray recording data set of the X-ray recording having multiple data channels. In the applying step, a trained function is applied to the input data, wherein the trained function is based on a machine learning method, wherein the trained function is applied to at least two data channels with regard to determining the abnormal structure and wherein output data is generated. In the providing step, output data is provided, wherein the output data comprises an abnormal structure of the examination region.

The determination can also be referred to as finding, specifying, evaluating or providing. The abnormal structure can also be referred to as a diagnostically relevant characteristic. The abnormal structure can be for example a suspicious region or the probability for the existence of a dedicated discovery or finding.

The inventors have recognized that via energy-resolved X-ray detectors it is possible to improve the accuracy of AI-based CAD algorithms via the complementary information received in for example different detection layers or detection channels.

The X-ray system, for example with application in computer tomography, angiography, mammography, fluoroscopy or radiography can comprise a counting direct converting X-ray detector or a multi-layered X-ray detector. Both the counting X-ray detector as well as the multi-layered X-ray detector can comprise multiple data channels as an output. The trained function can be adapted to an X-ray detector, in particular to the characteristics of the X-ray detector.

The inventors propose to utilize the information that is recorded in the various detection layers or data channels simultaneously for AI-based CAD algorithms or the trained function.

The method can in this case comprise the following steps. It is possible via the multi-layered X-ray detector or the counting X-ray detector to generate N, in particular two dimensional, recording image data sets or an X-ray recording image data set using N channels in a step of the X-ray recording. The recording image data sets or the X-ray recording image data set can either be generated by the X-ray detector itself or additional recording image data sets can be calculated or generated based on a recombination of output information, in particular in various data channels. The N recording image data sets or the X-ray recording image data set having N channels can be used as input data for the trained function. In the receiving step, input data is received, wherein the input data relates to an X-ray recording data set of the X-ray recording having multiple data channels or multiple recording image data sets. For example, it is possible using a multi-layered X-ray detector or a counting X-ray detector N to record detector images or an X-ray recording data set having N channels. These N detector images or the X-ray recording data set having the N channels can be used as input data for the trained function, in particular an AI-based CAD algorithm.

In the applying step, a trained function is applied to the input data. The trained function is based on a machine learning method. In general, a trained function can understand cognitive functions that can be associated with a human brain. In particular, during training based on training data the trained function can be adapted to new boundary conditions and can identify and extrapolate patterns.

In general, parameters of a trained or trainable function can be adapted via training. It is possible to use in particular a monitored, part-monitored, unmonitored, reinforced learning or active learning. Moreover, so-called "representation learning" can be used. In particular, the parameters of the trained function can be adapted in an iterative manner in multiple steps of the training.

In particular, a trained function can comprise a neural network, a support vector machine, a decision tree or a Bayesian network, and/or the trained function can be based on so-called k means clustering, Q learning, genetic algorithms and/or association rules. In particular, the neural network can be a so-called deep neural network, a convolutional neural network or a convolutional deep neural network. Moreover, the neural network can be a so-called adversarial network, a deep adversarial network and/or a generative adversarial network.

The trained function can be based on a monitored learning method. The trained function can be based on a machine learning method. The trained function can be based in particular on a neural network. It is possible to use above all annotated input training data and output training data for the training. It is preferably possible to use a deep learning method. Alternatively, it is possible to use a machine learning method. The features can be extracted manually or preferably by machine. Feed forward neural networks, recurrent neural networks (RNN) or preferably convolutional neural networks (CNN) can be used as a neural network. Advantageously, via the monitored learning method relationships can be concluded between the input training data and output training data and applied to input data.

Machine learning in the sense of one or more example embodiments of the present invention comprises a computer-implemented technique in which an algorithm identifies patterns or regularities on the basis of existing data and using the same patterns or regularities autonomously derives solutions in relation to unknown new data. A requirement for an autonomous search for solutions is a training phase in which an algorithm of the machine learning is applied to a known defined and for the most part large database in order to find rules or forecasts that achieve a desired output or a desired result. The training can be designed as monitored or unmonitored training, wherein in the first variant value pairs in the form of input training data and correct output training data that is associated therewith are presented to the algorithm whereas in the second variant the algorithm must itself adapt autonomously based on the input training data in such a manner that the algorithm provides the correct output training data.

The algorithm of the machine learning is particularly advantageously designed as an artificial neural network. An artificial neural network is based on building a biological neural network such as for example a human brain. An artificial neural network preferably comprises between an input layer and an output layer a plurality of further layers in each case comprising at least one node. Each node corresponds in this case to a processing unit, in a similar manner to a biological neuron. Nodes within a layer of the network can be connected via directional connections or edges to nodes of other layers. The connections define the data flow within the network. Each node consequently represents an operation that is applied to the input data. Moreover, each node or each of its connections has at least one weighting parameter. The influence or the weighting of the output of a node is defined via this weighting parameter or these weighting parameters as an input value for a receiver node. In the training phase, which is preferably performed as monitored learning, the artificial neural network "learns" with the aid of the training data the weighting parameters for all the nodes or connections and adapts these until the output layer of the network provides the correct output data or output training data.

The approach in accordance with one or more example embodiments of the present invention moreover relates to the knowledge that a trained algorithm of the machine learning during its training produces a fixed relationship between input data sets, here input training data related to an X-ray recording data set having multiple data channels, and output values, here an abnormal structure of the examination region.

In one embodiment, the trained function can be based on a so-called deep learning method. For example, it is also possible to use a "convolutional neural network". In other words, in accordance with this embodiment via an algorithm of the machine learning initially a feature extraction is performed and subsequently a so-called classification or regression, wherein the identified features in relation to the data channels can be allocated to an abnormal structure of the examination region. In the case of a classification, the probabilities can lie between 0 and 1. In the case of a regression, it is possible to use continuous values, for example coordinates in the image for the description of a suspect region or an abnormal structure. As an alternative to a convolutional neural network it is also possible to use long short-term memory (LSTM) networks or recurrent neural networks (RNN) that have in contrast to the above mentioned backwards oriented feedback loops within the hidden network layers.

The trained function can be applied to at least two data channels or two recording image data sets with regard to determining the abnormal structure. Output data is generated. In the providing step, the output data is provided, wherein the output data comprises an abnormal structure of the examination region.

Advantageously, it is possible to simultaneously or in parallel or at the same time use the complementary information that is recorded in the different layers of the multi-layered X-ray detector or the different energy channels of the counting X-ray detector as input data for the trained function. Advantageously, it is possible to simultaneously or in parallel or at the same time derive spectral or material-resolving information or based on a recombination of detector output images or recording data sets said information can be used as input data for the trained function.

In accordance with one aspect of one or more example embodiments of the present invention, an, in particular two-dimensional, recording image data set is provided for each data channel. For a layer of the multi-layered X-ray detector, it is possible to also provide a two-dimensional recording image data set. The multi-layered X-ray detector can have a matrix of detection elements in each layer. The detection elements can be designed as identical or as different in size in the different layers. In the case of detection elements that are designed as different in size in the different layers, it is possible to apply a rebinning procedure prior to the trained function being applied to the input data. One layer can, in particular precisely, refer to one data channel.

It is possible to provide a two-dimensional recording image data set for an energy channel of a counting X-ray detector. The counting X-ray detector can have a matrix of detection elements for each energy channel. The detection elements can be designed in the different energy channels as identical or different in size. In the case of detection elements that are designed as different in size in the different energy channels, it is possible to apply a rebinning procedure prior to the trained function being applied to the input data. One energy channel can, in particular precisely, refer to one data channel. Advantageously, the spectrally-different or spectrally-complementary information can be used for an improved recognition of an abnormal structure in the examination region.

In accordance with one aspect of one or more example embodiments of the present invention, the data channels relate to data sets that are different from one another from the group of: a soft part data set, a bone data set, a native image data set, a contrast medium data set, an energy region data set or multiple energy region data sets that are different from one another.

The soft part data set or the bone data set can be generated based on a material breakdown and thereby a recombination of information from various data channels. The contrast medium data set can be generated based on a recording using a contrast medium, where applicable using two different X-ray spectra during the recording. The native image data set can comprise for example the information from multiple or all the data channels and can represent in particular a "normal" X-ray image.

The energy region data set can relate to an energy channel of a counting X-ray detector. The energy region data set can relate to a layer of a multi-layered X-ray detector. Multiple energy region data sets that are different from one another can relate in particular to disjointed energy region. Multiple energy region data sets that are different from one another can relate to overlapping energy regions. Advantageously, an item of spectral information can be used to determine abnormal structures.

In accordance with one aspect of one or more example embodiments of the present invention, the X-ray recording data set is recorded using a multi-layered X-ray detector or a photon-counting X-ray detector. The photon-counting X-ray detector can also be referred to as a counting X-ray detector. Advantageously, spectral information can be recorded via an X-ray recording.

In accordance with one aspect of one or more example embodiments of the present invention, the input data comprises: complementary information in the data channels, spectral or material-resolving information or/and information based on a recombination of image data of the data channels.

In particular, in the case of the use of a soft part data set, a bone data set, a native image data set (in particular minus an item of contrast medium information), a contrast medium data set, an energy region data set or multiple energy region data sets that are different from one another, complementary information, spectral or material-resolving information and/or information based on a recombination of image data of the data channels can be used by the trained function in order to render it possible to better determine an abnormal structure. The material-resolving information can relate for example to a soft part data set and a bone data set. The complementary spectral information can relate for example to an energy region data set or to multiple energy region data sets that are different from one another. The recombination of image data of the data channels can relate for example to a native image data set.

In accordance with one aspect of one or more example embodiments of the present invention, the trained function is applied to the at least two data channels simultaneously. It is possible in particular to apply a trained function, in other words for example a neural network, to two data channels. Alternatively, a first trained function can be applied to a first data channel and a second trained function can be applied to a second data channel, in particular simultaneously or in parallel. Advantageously, despite the increased quantity of data in reference to the input data it is possible to rapidly generate output data.

In accordance with one aspect of one or more example embodiments of the present invention, the trained function is based on a deep learning method for RGB images. An example for the application of a method in accordance with one or more example embodiments of the present invention is the use of a deep learning model (DL model) or a deep learning method, in particular one that is optimized for RGB images or RGB image data. The deep learning method can be optimized in relation to RGB image data in order to extract information from the three input channels. In lieu of adapting the model in order to process only one image or to copy the same image into the three RGB channels, cf. in this regard: M. Chen, "Automated bone age classification with deep neural networks", 2016, http://cs231n.stanford.edu/reports/2016/pdfs/310_Report.pdf H. Lee, "Fully automated deep learning systems for bone age assessment", J Digit Imaging 2017, https://link.springer.com/article/10.1007/s10278-017-9955-8 S. Guendel et al.: "Learning to Recognize Abnormalities in Chest X-Rays with Location-Aware Dense Networks", CIARP 2018, https://arxiv.org/abs/1803.04565 Z. Li et al.: "Thoracic Disease Identification and Localization with Limited Supervision", CVPR 2018, https://arxiv.org/abs/1711.06373 the inventors have determined that a promising alternative is to use the X-ray recording data having multiple data channels, in particular a multi-layered X-ray detector or a photon-counting X-ray detector, in this case as input data of the DL model or the trained function. An existing or known RGB model can extract the information from three recording image data sets or three data channels, in particular a multi-layered X-ray detector or a photon-counting X-ray detector. For example, it is possible, based on the X-ray recording data set, to generate and provide as input data for the RGB model: a first recording image data set or a first data channel in relation to soft parts or soft tissues, a second recording image data set or second data channel in relation to bone structures and a third recording image data set or data channel in relation to a native image data set. The first data channel can be used for example for the R channel of the RGB model, the second data channel can be used for the G channel and the third data channel can be used for the B channel. Advantageously, it is possible to use an existing deep learning method.

In accordance with one aspect of one or more example embodiments of the present invention, three data channels are used. In particular, with regard to an RGB (DL) model it is possible to use the R, G and B channel.

In accordance with one aspect of one or more example embodiments of the present invention, prior to applying the trained function an image processing is applied to the X-ray recording data set. The image processing can comprise steps for recombining information of the data channels.

The image processing can comprise noise correction, intensity adaptation or artefact correction. Advantageously, it is possible by image processing, in particular image pre-processing to use the same trained function for example for different X-ray detectors or their X-ray recording data sets. The X-ray recording data set of a first X-ray detector can be adapted by the image processing in such a manner that the X-ray recording data set can have the same image characteristics as an X-ray recording data set of a second X-ray detector. Advantageously, it is possible to avoid an adaptation of the trained function to another X-ray detector.

In accordance with one aspect of one or more example embodiments of the present invention, the output data comprises as an abnormal structure a position of a lesion, a position of a microcalcification, a position of a landmark, a distance or an angle. The output data can comprise a coordinate within the X-ray recording data set. The output data can comprise a surface, a distance or an angle, in particular via coordinates within the X-ray recording data set. The output data can comprise in particular a location or position and expansion of an abnormal structure. Advantageously, it is possible via the output data to represent the abnormal structure in the X-ray recording data set. Advantageously, it is possible via the output data to store the abnormal structure, for example in a DICOM data set, in particular as a secondary capture.

Moreover, one or more example embodiments of the present invention relates to a computer-implemented method for providing a trained function for an X-ray system having:
  receiving input training data, wherein the input training data relates to an X-ray recording data set of an X-ray recording having multiple data channels,
  receiving output training data, wherein the output training data is connected to the input training data and wherein the output training data comprises an annotation of the X-ray recording or the X-ray recording data set having an abnormal structure of the examination region,
  training a trained function based on the input training data and the output training data providing the trained function.

In the training step, a trained function is trained based on the input training data and the output training data using a training computing unit. The training can include that initially preliminary output data is determined by applying the trained function to the input training data and the trained function is adapted based on the comparison between the initially preliminary output data and the output training data.

The trained function can be already trained. The trained function can alternatively not yet be trained. The trained function can be a not yet trained function. The method in accordance with one or more example embodiments of the present invention can comprise further training of the trained function. For example, the training can be designed as an adaptation step or adaptation training to the input training data and the output training data of the X-ray detector. The trained function can be (pre)trained using training data of at least one other X-ray detector and subsequently can be adapted in the training step to the X-ray detector.

Moreover, one or more example embodiments of the present invention relates to a computer-implemented method in accordance with one or more example embodiments of the present invention, wherein the trained function is provided by the computer-implemented method in accordance with one or more example embodiments of the present invention so as to provide a trained function for an X-ray system in order to determine an abnormal structure of the examination region in an X-ray recording.

Moreover, one or more example embodiments of the present invention can relate to a training system having:
  a first training interface for receiving input training data, wherein the input training data relates to an X-ray recording data set of an X-ray recording having multiple data channels,
  a second training interface for receiving output training data, the output training data being connected to the input training data and wherein the output training data comprises an annotation of the X-ray recording having an abnormal structure of the examination region,
  a training computing unit for training a function based on the input training data and the output training data,
  a third training interface for providing the trained function.

In a particularly advantageous embodiment, the X-ray system or the determining apparatus can comprise the training system. Alternatively, the training system can be connected via a network to the X-ray system or the determining apparatus. Advantageously, the trained function can be adapted to the X-ray detector. It is particularly preferred that the trained function can be further adapted to the X-ray detector by adapting with new input training data and output training data.

Moreover, one or more example embodiments of the present invention relates to a determining apparatus for implementing a method in accordance with one or more example embodiments of the present invention having:
  a first interface for receiving input data, wherein the input data relates to an X-ray recording data set of the X-ray recording having multiple data channels,
  a computer unit for applying a trained function to at least two data channels with regard to determining the abnormal structure, wherein output data is generated and wherein the trained function is based on a machine learning method, a second interface for providing output data, wherein the output data comprises an abnormal structure of the examination region.

The X-ray system can comprise the determining apparatus. Alternatively, the determining apparatus can be a system that is remote from the X-ray system, for example the method in accordance with one or more example embodiments of the present invention can be implemented via a cloud-based data network. In this regard, the X-ray recording data set can be transmitted via a data connection to the determining apparatus, in particular outside of the clinical network, where it is possible to implement the method in accordance with one or more example embodiments of the present invention in the determining apparatus and the output data can be relayed back into the clinical network or another desired receiver.

Moreover, one or more example embodiments of the present invention relates to an X-ray system having a determining apparatus in accordance with one or more example embodiments of the present invention. The X-ray system can have in particular an X-ray source and an X-ray detector. The examination object having the examination region can be arranged between the X-ray source and the X-ray detector. In the case of an X-ray recording it is possible to generate an X-ray recording data set. This can comprise further data in addition to the X-ray recording or the X-ray image, for example recording parameters. Moreover, the X-ray system can comprise a display unit, for example a screen, for displaying the output data. Moreover, the X-ray system can comprise an input unit, for example a keyboard, mouse or another touch-sensitive input unit for inputting user inputs.

Moreover, one or more example embodiments of the present invention relates to a computer program product having a computer program that can be loaded directly into a storage facility of a control facility of a determining apparatus in accordance with one or more example embodiments of the present invention or an X-ray system in accordance with one or more example embodiments of the present invention and the computer program product has program sections in order to perform all the steps of a method in accordance with one or more example embodiments of the present invention if the computer program is executed in the control facility of the X-ray system.

FIG. 1 illustrates an exemplary embodiment of a method 10 in accordance with the invention in a first embodiment. The computer-implemented method 10 for determining an abnormal structure in an examination region in conjunction with an X-ray recording of an X-ray system has the steps of receiving 12, applying 13 and providing 14. In an optional recording step 11, it is possible to record the X-ray recording data set. The X-ray recording data set is recorded using a multi-layered X-ray detector or a photon-counting X-ray detector. In the receiving step 12, the input data is received, wherein the input data relates to an X-ray recording data set of the X-ray recording having multiple data channels. In the applying step 13, a trained function is applied to the input data, wherein the trained function is based on a machine learning method, wherein the trained function is applied to at least two data channels with regard to determining the abnormal structure, and wherein output data is generated. In the providing step 14, the output data is provided, wherein the output data comprises an abnormal structure of the examination region.

It is possible to provide an, in particular two dimensional, recording image data set for each data channel. The various data channels can relate to data sets that are different from one another from the group of: a soft part data set, a bone data set, a native image data set, a contrast medium data set, an energy region data set or multiple energy region data sets that are different from one another. The input data comprises complementary information in the data channels, spectral or material-resolving information or/and information based on a recombination of image data of the data channels. In one preferred embodiment, the trained function is applied to the at least two data channels simultaneously. The output data comprises as an abnormal structure a position of a lesion, a position of a microcalcification, a position of a landmark, a distance or an angle.

Figure 2:
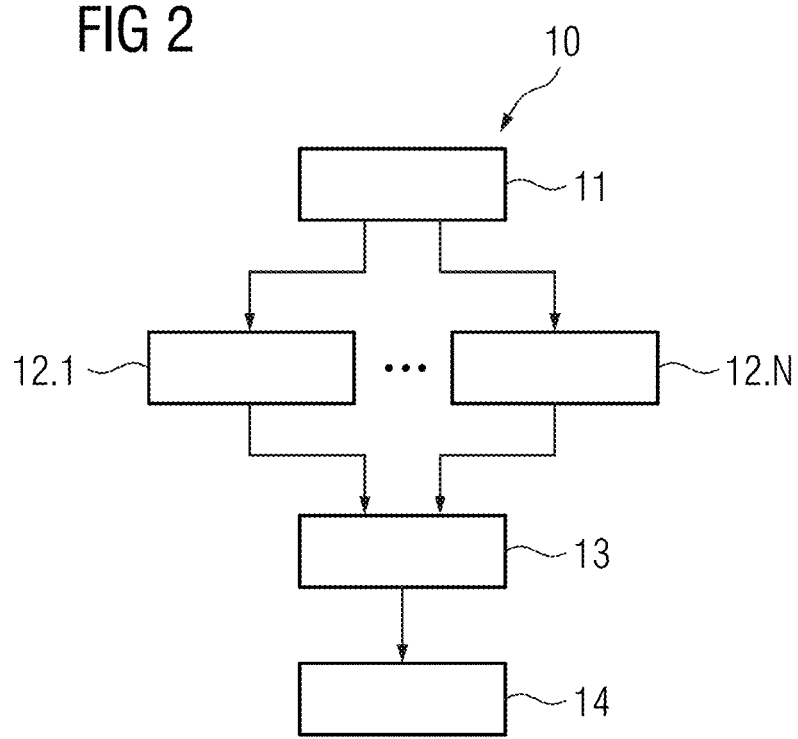
FIG. 2 shows schematically an illustration of a method in accordance with the invention in a second embodiment.

FIG. 2 illustrates an exemplary embodiment of a method 10 in accordance with the invention in a second embodiment. In step 11, it is possible via a multi-layered X-ray detector or a photon-counting X-ray detector to record the X-ray recording data set. The X-ray recording data set has multiple data channels or multiple two-dimensional recording image data sets. In the receiving step 12.1, the information of a first data channel or of the first recording image data set is received as input data. In the receiving step 12.N, the information of an N-th data channel or of the N-th recording image data set is received as input data. In the applying step 13, the trained function or at least a trained function is applied to the input data and output data is generated. In a step 14, the output data is provided.

Figure 3:
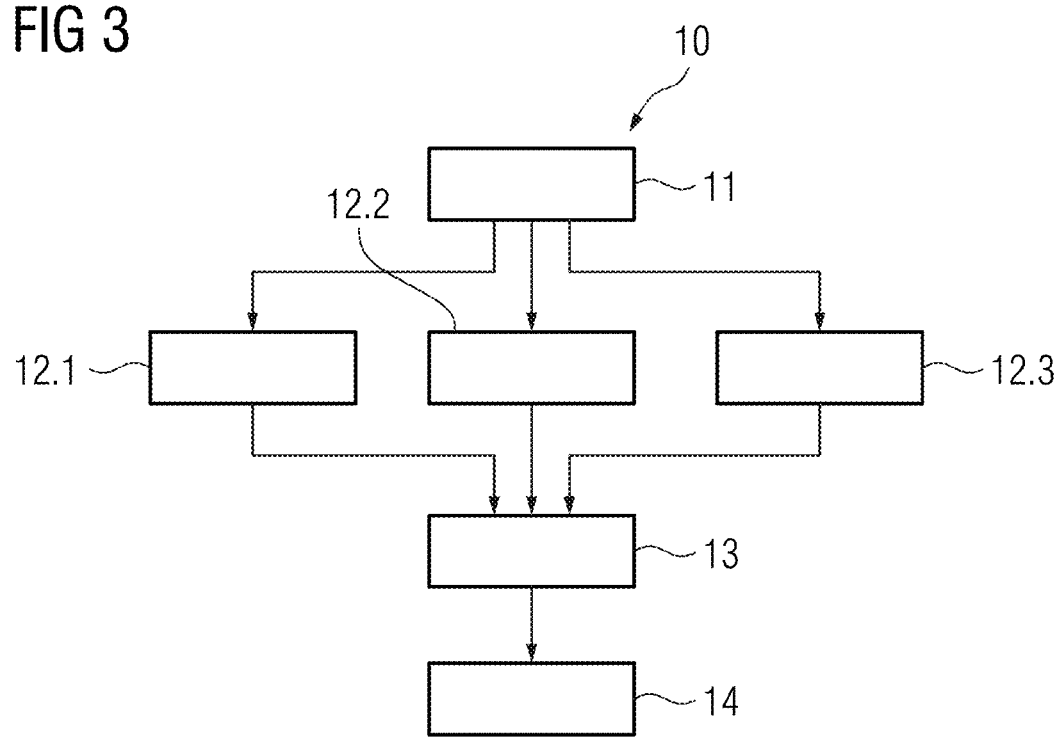
FIG. 3 shows schematically an illustration of a method in accordance with the invention in a third embodiment.

FIG. 3 illustrates an exemplary embodiment of a method 10 in accordance with the invention in a third embodiment. The trained function is based on an RGB model. The trained function is based on a deep learning method for RGB images. Three data channels are used. In the receiving step 12.1, a first data channel or a first recording image data set, in particular a soft part data set, is received and the first data channel is allocated to the R channel. In the receiving step 12.2, a second data channel or a second recording image data set, in particular a bone data set, is received and the second data channel is allocated to the G channel. In the receiving step 12.3, a third data channel or a third recording image data set, in particular a native image data set, is received and the third data channel is allocated to the B channel. It is possible to use the three recording image data sets, which have been generated based on an X-ray recording data set of a multi-layered X-ray detector or of a photon-counting X-ray detector, as input channels or input data of an RGB model for an AI-based CAD algorithm or such a trained function.

Figure 4:
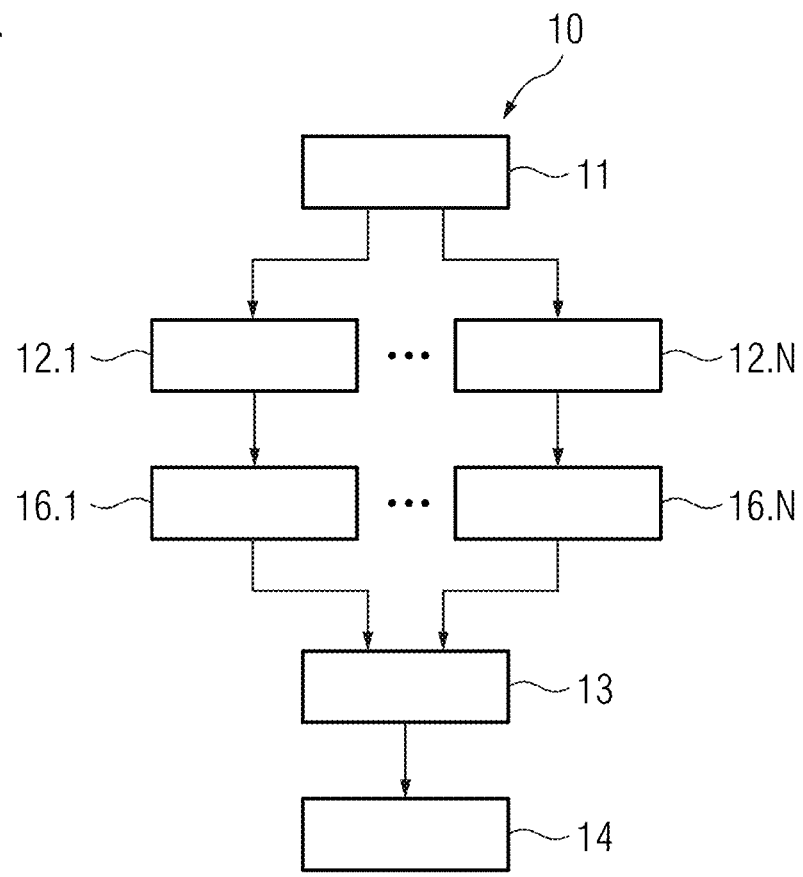
FIG. 4 shows schematically an illustration of a method in accordance with the invention in a fourth embodiment.

FIG. 4 illustrates an exemplary embodiment of a method 10 in accordance with the invention in a fourth embodiment. Prior to the application 13 of the trained function, an image processing 16.1, . . . , 16.N is applied to the X-ray recording data set. In this case, the image processing is applied in particular separately to each data channel. The extracted recording image data sets or information of the data channels can be modified via image processing prior to the recording image data sets or information of the data channels being used as input data for the trained function.

Figure 5:
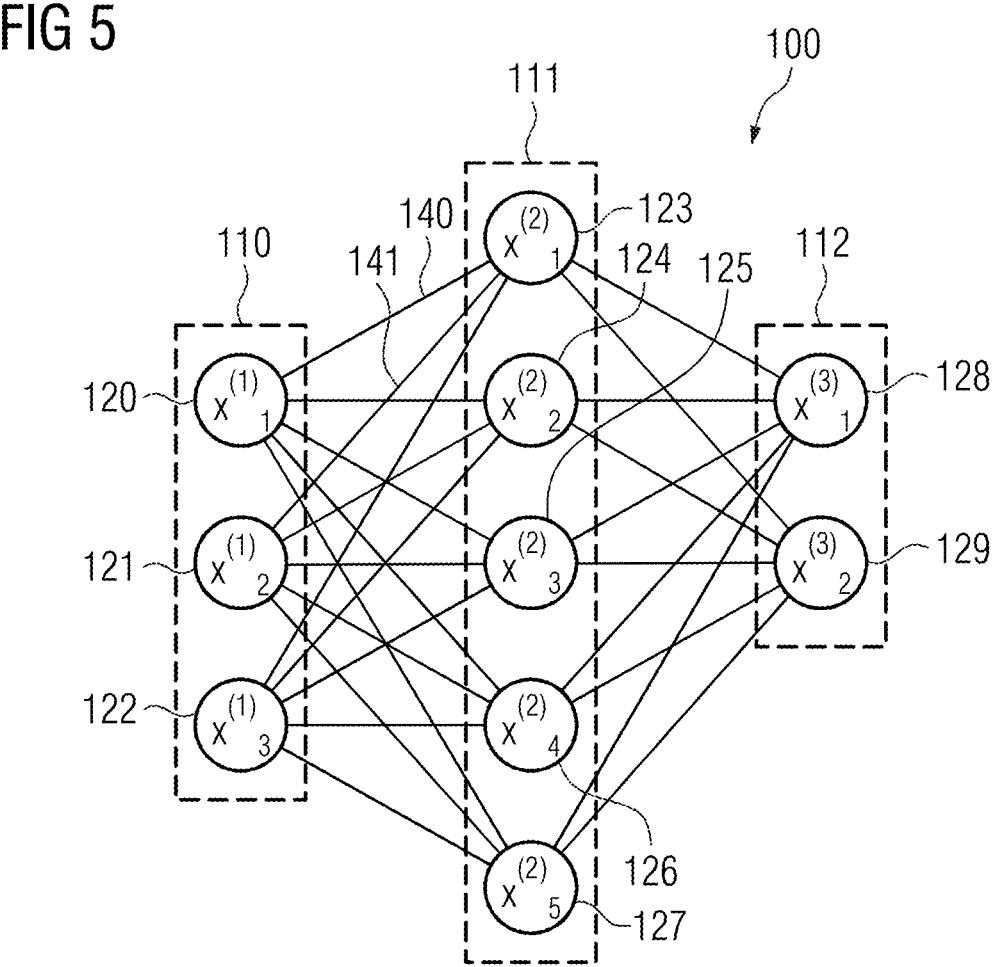
FIG. 5 shows schematically an illustration of an artificial neural network in accordance with the invention.

FIG. 5 illustrates an artificial neural network 100 such as can be used in the method in accordance with FIGS. 1 to 4. The neural network can also be referred to as an artificial neural network or neural network.

The neural network 100 comprises nodes 120, . . . , 129 and edges 140, 141, wherein each edge 140, 141 is a directional connection from a first node 120, . . . , 129 to a second node 120, . . . , 129. In general, the first node 120, . . . , 129 and the second node 120, . . . , 129 are different nodes, it is also possible that the first node 120, . . . , 129 and the second node 120, . . . , 129 are identical. An edge 140, 141 of a first node 120, . . . , 129 to a second node 120, . . . , 129, can also be referred to as an inbound edge for the second node and as an outbound edge for the first node 120, . . . , 129.

The neural network 100 responds to input values x(1)1, x(1)2, x(1)3 to a plurality of input nodes 120, 121, 122 of the input layer 110. The input values x(1)1, x(1)2, x(1)3 are applied in order to generate one or a plurality of outputs x(3)1, x(3)2. The node 120 is connected for example via an edge 140 to the node 123. The node 121 is connected for example via the edge 141 to the node 123.

The neural network 100 learns in this exemplary embodiment in that it adapts the weighting factors (wi, j (weightings) of the individual nodes based on training data. Possible input values x(1)1, x(1)2, x(1)3 of the input nodes 120, 121, 122 can be for example attenuation values above a threshold that has been extracted beforehand from an X-ray recording data set of the X-ray recording, in particular a data channel. Alternatively, the input values can be the X-ray recording data set of the X-ray recording or the data channels themselves, in particular if the neural network 100 is designed to also perform the feature extraction. It is possible to use arbitrary other input values.

The neural network 100 weights the input values of the input layer 110 based on the learning process. The output values of the output layer 112 of the neural network 100 preferably correspond to an abnormal structure, for example with regard to the type and/or position. The output can be performed via an individual or a plurality of output nodes x(3)1, x(3)2 in the output layer 112.

The artificial neural network 100 preferably comprises a hidden layer 111 that comprises a plurality of nodes x(2)1, x(2)2, x(2)3. It is possible that multiple hidden layers are provided, wherein a hidden layer uses output values of another hidden layer as input values. The nodes of a hidden layer 111 execute mathematical operations. An output value of a node x(2)1, x(2)2, x(2)3 corresponds in this case to a non-linear function f of its input values x(1)1, x(1)2, x(1)3 and the weighting factors wi, j. After obtaining input values x(1)1, x(1)2, x(1)3 a node x(2)1, x(2)2, x(2)3 performs a summation of a multiplication of each input value x(1)1, x(1)2, x(1)3 which is weighted with the weighting factors wi, j, as is determined by the following function:

$$x_j^{(n+1)} = f\left(\sum_i x_i^{(n)} \cdot w_{i,j}^{(n)}\right).$$

The weighting factor wi, j can be in particular a real number, in particular can lie in the interval of [−1; 1] or [0; 1]. The weighting factor $w_{i,j}^{(m,n)}$ refers to the weighting of the edge between the i-th node or an m-th layer 110, 11, 112 and a j-th node of the n-th layer 110, 111, 112. The weighting factor $w_{i,j}^{(m,n)}$ is an abbreviation for the weighting factor $w_{i,j}^{(n,n+1)}$.

In particular, an output value of a node x(2)1, x(2)2, x(2)3 is formed as a function f of a node activation, for example a sigmoid function or a linear ramp function. The output values x(2)1, x(2)2, x(2)3 are transmitted to the output node or nodes 128, 129. A summation of a weighted multiplication of each output value x(2)1, x(2)2, x(2)3 is again performed as a function of the node activation f and thereby calculates the output values x(3)1, x(3)2.

The neural network 100 that is illustrated here is a feedforward neural network in which all the nodes 111 process the output values of a previous layer in the form of their weighted sum as input values. Of course, in accordance with one or more example embodiments of the present invention other neural network types can also be used, for example feedback networks in which an input value of a node can be simultaneously also its output value.

The neural network 100 is trained via a method of monitored learning in order to identify patterns. A known approach is back propagation that can be applied for all the exemplary embodiments of the invention. During the training, the neural network 100 is applied to input training data or input training values and must generate corresponding, previously known output training data or output training values. Mean square errors "MSE" between calculated and expected output values are calculated in an iterative manner and individual weighting factors are thus adapted until the deviation between the calculated and expected output values is below a predetermined threshold.

Figure 6:
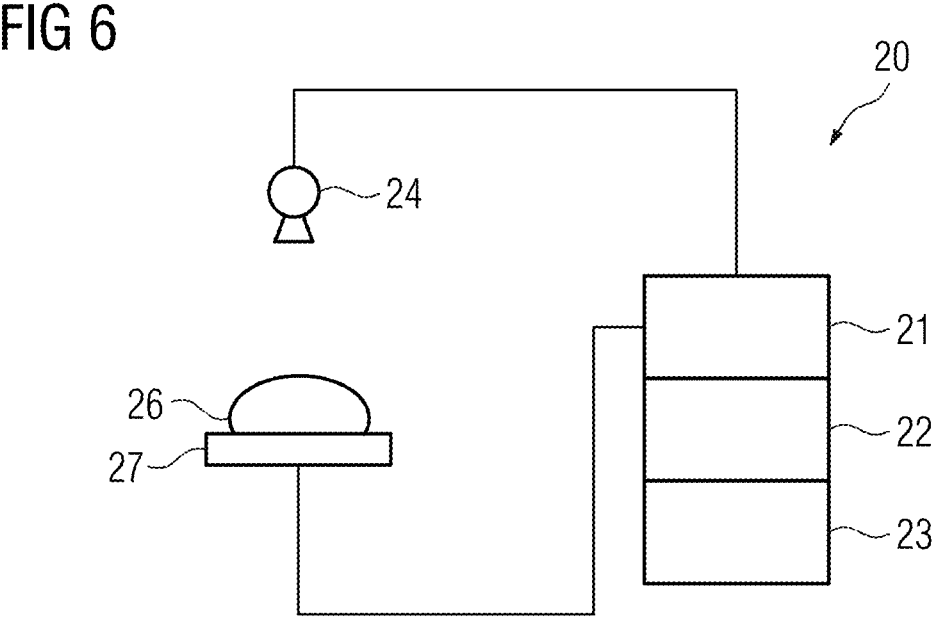
FIG. 6 shows schematically an illustration of an X-ray system in accordance with the invention.

FIG. 6 illustrates an exemplary embodiment of an X-ray system 20 in accordance with one or more example embodiments of the present invention. The X-ray system 20 comprises an X-ray source 24 and an X-ray detector 27 between which the examination object 26 having the examination region is arranged. The X-ray detector 27 can be designed in particular as a multi-layered X-ray detector or as a photon-counting X-ray detector. The X-ray system 20 has a determining apparatus in accordance with one or more example embodiments of the present invention. The determining apparatus for implementing a method in accordance with one or more example embodiments of the present invention has a first interface 21 for receiving input data, wherein the input data relates to an X-ray recording data set of the X-ray recording having multiple data channels. Moreover, the determining apparatus has a computer unit 22 for applying a trained function to at least two data channels with regard to a determination of the abnormal structure, wherein output data is generated and wherein the trained function is based on a machine learning method. Moreover, the determining apparatus has a second interface 23 for providing output data, wherein the output data comprises an abnormal structure of the examination region. The first and the second interface can also be a common interface.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particular manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module', 'interface' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing system or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the invention has been further illustrated in detail by example embodiments, the invention is not limited in this manner by the disclosed examples and other variations can be derived therefrom without departing from the protective scope of the invention.

We claim:

1. A determining apparatus configured to determine an abnormal structure in an examination region in conjunction with an X-ray recording of an X-ray system, the determining apparatus comprising:
   a first interface configured to receive input data, the input data relating to an X-ray recording data set of the X-ray recording having multiple data channels and including at least one of complementary information in the multiple data channels, spectral or material-resolving information, or information based on a recombination of image data of the multiple data channels;
   a computer unit configured to apply a trained function to at least two data channels to determine the abnormal structure and generate output data, the trained function being based on a machine learning method; and
   a second interface configured to provide the output data, the output data including the abnormal structure of the examination region.

2. An X-ray system having the determining apparatus of claim 1.

3. A computer-implemented method for determining an abnormal structure in an examination region in conjunction with an X-ray recording of an X-ray system, the method comprising:
   receiving input data, the input data relating to an X-ray recording data set of the X-ray recording having multiple data channels and including at least one of complementary information in the multiple data channels, spectral or material-resolving information, or information based on a recombination of image data of the multiple data channels;
   applying a trained function to the input data, the trained function being based on a machine learning method and applied to at least two data channels to determine the abnormal structure and generate output data; and
   providing the output data, the output data including an abnormal structure of the examination region.

4. The method of claim 3, the receiving the input data includes,
   providing a recording image data set for each data channel of the multiple data channels.

5. The method of claim 4, wherein the multiple data channels relate to data sets that are different from one another from a group of:
   a soft part data set, a bone data set, a native image data set, a contrast medium data set, an energy region data set, or multiple energy region data sets that are different from one another.

6. The method of claim 5, wherein the output data comprises a position of a lesion, a position of a microcalcification, a position of a landmark, a distance or an angle.

7. The method of claim 3, wherein the multiple data channels relate to data sets that are different from one another from a group of:
   a soft part data set, a bone data set, a native image data set, a contrast medium data set, an energy region data set, or multiple energy region data sets that are different from one another.

8. The method of claim 3, wherein the X-ray recording data set is recorded using a multi-layered X-ray detector or a photon-counting X-ray detector.

9. The method of claim 3, wherein the applying applies the trained function to the at least two data channels simultaneously.

10. The method of claim 3, wherein the trained function is based on a deep learning method for red-green-blue (RGB) images.

11. The method of claim 3, wherein three data channels are used.

12. The method of claim 3, further comprising:
   applying image processing to the X-ray recording data set prior to applying the trained function.

13. The method of claim 3, wherein the output data comprises a position of a lesion, a position of a microcalcification, a position of a landmark, a distance or an angle.

14. A non-transitory computer program product having a computer program that, when executed by a control facility of an X-ray system, are configured to cause the X-ray system to perform the method of claim 3.

15. A non-transitory computer readable medium having program sections that, when executed by a computer unit, cause the computer unit to perform the method of claim 3.

* * * * *